US00PP19485P2

(12) United States Plant Patent
Zary

(10) Patent No.: US PP19,485 P2
(45) Date of Patent: Nov. 25, 2008

(54) MINIATURE ROSE PLANT NAMED 'JACDANDY'

(50) Latin Name: *Rosa hybrida*
Varietal Denomination: JACdandy

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,353

(22) Filed: Nov. 28, 2007

(51) Int. Cl.
*A01H 5/00* (2006.01)

(52) U.S. Cl. ..... Plt./121

(58) Field of Classification Search ..... Plt./121
See application file for complete search history.

*Primary Examiner*—Kent L. Bell
*Assistant Examiner*—Georgia Helmer
(74) *Attorney, Agent, or Firm*—Klarquist Sparkman, LLP

(57) ABSTRACT

Miniature rose plant having novel lavender pink and brown flower color; compact, well-branched plant habit of growth; ease of own root rooting from soft wood cuttings; and resistance to rust and powdery mildew.

1 Drawing Sheet

Genus and species: *Rosa hybrida.*
Variety denomination: 'JACdandy'.

ORIGIN OF THE INVENTION

The present invention relates to a new and distinct variety of a miniature rose plant named 'JACdandy' which was originated by me by crossing the rose plant 'JACbow' (U.S. Plant Pat. No. 11,690, seed parent) with the rose plant 'Chipmunk' (unpatented, pollen parent).

BACKGROUND OF THE INVENTION

The primary objective of this breeding was to produce a new miniature rose variety having the vigor and own root capabilities of the female parent combined with the small flowers and foliage of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Novel lavender pink and brown flower color.
2. Compact, well-branched plant habit of growth.
3. Ease of own root rooting from soft wood cuttings.
4. Resistance to rust and powdery mildew.

Asexual reproduction of this new variety by cuttings, as performed at Wasco and Somis, Calif., shows that the foregoing and all other characteristics and distinctions come true to form and are established and transmitted through succeeding propagations.

COMPARISON WITH PARENTS

'JACdandy' differs from the female parent 'JACbow' in having smaller flowers (about 7 to 7.5 cm open diameter for 'JACbow' versus about 4 cm open diameter for 'JACdandy'). 'JACdandy' differs from the male parent 'Chipmunk' in being much larger (about 60–80 cm high and 60–70 cm wide when mature for 'JACdandy' versus about 30 cm for 'Chipmunk'). 'JACdandy' also has less fragrance than 'Chipmunk'.

COMPARISON WITH SIMILAR VARIETY

Either 'JACbow' (U.S. Plant Pat. No. 11,690) or 'Chipmunk' (unpatented) is the most similar variety to 'JACdandy' known to the inventor.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivator with color descriptions using terminology in accordance with The Royal Horticultural Society (London) Colour Chart© 2001, except where ordinary dictionary significance of color is indicated.

Parentage:
*Seed parent.*—'JACbow' (U.S. Plant Pat. No. 11,690).
*Pollen parent.*—'Chipmunk' (unpatented), Observations were made from January 2006 to October 2007 of plants of the new variety grown in a garden environment in Somis, Calif. The observations below are of three year old plants.

FLOWER

Blooming habit: Continuous.
Bud:
*Size.*—About 10 mm long and 13 mm in diameter when the petals start to unfurl.
*Form.*—The bud form is short, pointed ovoid.

*Color.*—When sepals first divide, bud color is Greyed-Purple Group 186D. When half blown, the upper sides of the petals are Greyed-Purple Group 186D on outer petals changing to Greyed-Purple Group 183D in the middle rows of petals to Greyed-Orange Group 174D in the center of the flower; and the lower sides of the petals are Greyed-Purple Group 186D on the outer petals changing to Greyed-Orange Group N170C in the center petals.

*Sepals.*—Color: Upper surface: Green Group 138B. Lower surface: Yellow-Green Group 146C, but in bright sun can be overlain with Greyed-Purple Group 183A. Length: 18–20 mm. Width: 6–7 mm. Shape: Subulate. Surface: Hoary. There are three normally to heavily appendaged sepals. There are two unappendaged sepals with hairy edges.

*Receptacle.*—Color: Yellow-Green Group 146C. Shape: Funnel. Size: Small, about 8 mm long×7 mm wide. Surface: Smooth.

*Peduncle.*—Length: Short, averaging about 20–25 mm. Surface: Smooth with a few glands. Color: Yellow-Green Group 146C with Greyed-Purple Group 183D in areas exposed to bright sun. Strength: Stiff, erect.

Bloom:

*Size.*—Small. Average open diameter is about 4 cm.

*Borne.*—Singly and several together in rounded clusters of 3–5 blooms having flat shape.

*Stems.*—Strength: Strong. Average length is about 20–30 cm with a diameter of 3–4 mm.

*Form.*—When first open: High centered. Permanence: All petals curl with moderate quilling.

*Petalage.*—Number of petals under normal conditions: 25.

*Color.*—The upper sides of the petals are Greyed-Purple Group 186D on the outer petals changing to Greyed-Red Group 183D in the middle rows of petals and to Greyed-Orange Group 174D in the flower center. The reverse sides of the petals are Greyed-Purple Group 186D on the outer petals changing to Greyed-Orange Group N170C in the center petals. The base of the petals has a 5 mm×5 mm color spot of Yellow Group 4D. The major color on the upper sides is Greyed-Purple Group 186D.

*Variegations.*—None observed.

*Discoloration.*—The general tonality at the end of the first day: No change. At the end of the third day: A gradual color intensification to Red-Purple Group 60C. Further aging: By day 5, the entire flower becomes Red-Purple Group 60C.

*Fragrance.*—Slight, spicy.

Petals:

*Thickness.*—Thick.

*Shape.*—Orbicular.

*Surface texture.*—Smooth.

*Margin.*—Entire. Apex shape: Rounded. Base shape: Rounded.

*Form.*—Tips slightly recurved, edges slightly quilled.

*Arrangement.*—Imbricated.

*Petaloids.*—Number: 3–7. Size ranges from 3–11 mm long and 2–5 mm wide. Color: Greyed-Orange Group N170C.

*Persistence.*—Petals drop off cleanly before drying.

*Lastingness.*—On the plant: Long (about 6–7 days). As a cut flower: Long (about 8–9 days).

Reproductive parts:

*Stamens.*—Number: 60–70. Length: 5–6 mm. Anthers: Length: 1 mm. Color: Yellow-Orange Group 15A. Arrangement: Regular around styles. Filaments: Color: Yellow Group 13A. Length: 4–5 mm. Pollen: Color: Greyed-Orange Group 164B.

*Pistils.*—Number: 30–35. Length: 5–6 mm. Styles: Color: Greyed-Green Group 192B. Length: 4–5 mm. Stigmas: Color: Greyed-Yellow Group 161D. Length: 1 mm.

*Hips.*—Color: Yellow-Green Group 152D turning to Orange Group 28A when fully ripe. Shape: Globose. Size: 15 mm diameter, 14 mm top to bottom.

PLANT

*Form.*—Bush.

*Growth.*—Vigorous, dwarf, upright, branching, compact.

*Age at maturity.*—One year.

*Mature plant.*—Height: 60–80 cm. Width: 60–70 cm.

*Rootstock.*—Own root.

Foliage: Number of leaflets on normal mid-stem leaves: 5.

*Size.*—Small. About 65 mm long×40 mm wide.

*Quantity.*—Abundant.

*Color.*—New foliage: Upper side: Yellow-Green Group 152A. Lower side: Yellow-Green Group 152C. Old foliage: Upper side: Green Group 139A. Lower side: Yellow-Green Group 146C.

Leaflets:

*Size.*—About 17 mm long×14 mm wide.

*Shape.*—Pointed oval.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 146C.

*Petiole rachis.*—Color: Yellow-Green Group 146C. Underside: Smooth, with an occasional gland.

*Auricles.*—None observed.

*Stipules.*—Length: 10–11 mm; smooth.

*Disease resistance.*—Resistant to rust and mildew but susceptible to blackspot under normal growing conditions.

*Pest resistance.*—None observed.

*Vein color.*—Yellow-Green Group 146C.

*Venation pattern.*—Reticulate.

Wood:

*New wood.*—Color: Yellow-Green Group 144B. Bark: Smooth.

*Old wood.*—Color: Green Group 137C. Bark: Smooth.

Prickles:

*Quantity.*—Ordinary, on main canes from base: 9–10 per 15 cm. Ordinary, on laterals from main canes: 9–10 per 15 cm.

*Form.*—Hooked downward.

*Length.*—3 mm.

*Color when young.*—Greyed-Purple Group 183B.

*Color when mature.*—Greyed-Orange Group 165B.

Small prickles:

*Quantity.*—On main stalks: None. On laterals: None.

Winter hardiness: Hardy to Zone 5.

I claim:

1. A new and distinct variety of a rose plant of the miniature class, substantially as herein shown and described, characterized particularly by its novel lavender pink and brown flower color; compact, well-branched plant habit of growth; ease of own root rooting from soft wood cuttings; and resistance to rust and powdery mildew.

* * * * *

JACdandy
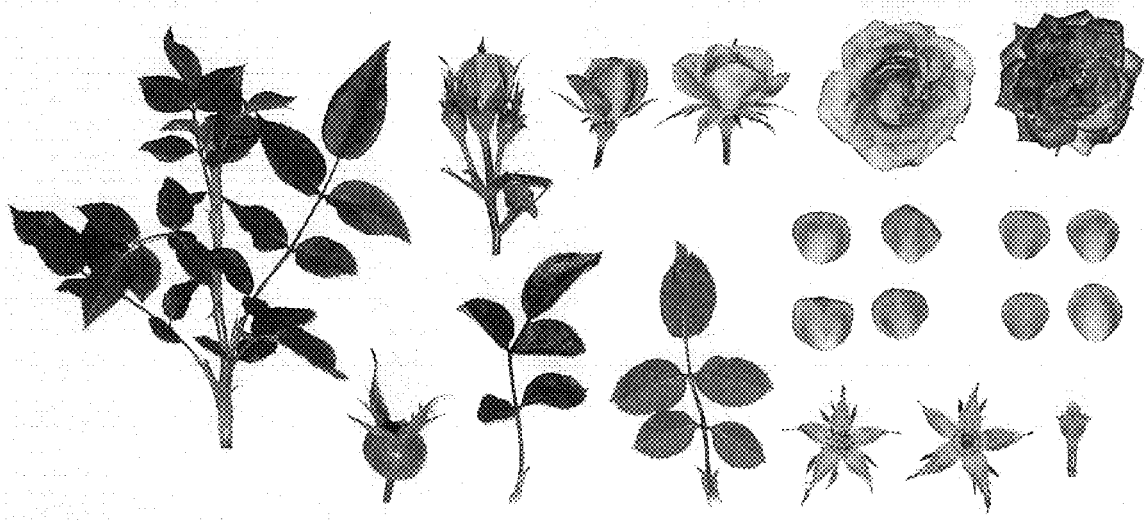

UNITED STATES PATENT AND TRADEMARK OFFICE

CERTIFICATE OF CORRECTION

PATENT NO. : PP 19,485 P2
APPLICATION NO. : 11/998353
DATED : November 25, 2008
INVENTOR(S) : Keith W. Zary It is certified that error appears in the above-identified patent and that said Letters Patent is hereby corrected as shown below:

In the Specification:

Column 2, Line 21; "cultivator" should read --cultivar--.

Signed and Sealed this

Ninth Day of June, 2009

JOHN DOLL
*Acting Director of the United States Patent and Trademark Office*